United States Patent [19]

Dragon et al.

[11] Patent Number: 4,870,006
[45] Date of Patent: Sep. 26, 1989

[54] ANTIGENIC MATERIAL FOR A CHAGAS' DISEASE DETECTION SYSTEM

[75] Inventors: Elizabeth A. Dragon, San Ramon; Stacey Sias, San Anselmo, both of Calif.

[73] Assignee: Codon, South San Francisco, Calif.

[21] Appl. No.: 926,982

[22] Filed: Nov. 4, 1986

Related U.S. Application Data

[63] Continuation-in-part of Ser. No. 889,419, Jul. 24, 1986.

[51] Int. Cl.[4] .................. C07K 15/04; G01N 33/531; G01N 33/546; G01N 33/569
[52] U.S. Cl. .......................................... 435/7; 435/810; 435/947; 436/518; 436/531; 436/533; 436/534; 436/536; 436/543; 436/808; 436/811; 530/350; 530/806; 530/808; 530/822; 935/47; 935/59
[58] Field of Search ................ 530/350, 806, 822, 808; 435/7, 947, 810; 436/543, 808, 811, 518, 531, 533–534, 536; 935/47, 59

[56] References Cited

U.S. PATENT DOCUMENTS

3,911,097 10/1975 Hanson .................................. 424/12
3,993,743 11/1976 Hanson .................................. 424/12

FOREIGN PATENT DOCUMENTS

0135108 3/1985 European Pat. Off. .
0138101 4/1985 European Pat. Off. .
8006951 10/1980 France .

OTHER PUBLICATIONS

Gonzales et al., Nucleic Acid Research, 13, 5789–5804, 1985.
Lizardi et al., Vaccines 85, Cold Spring Harbor Laboratory, pp. 67–70, 1985.
Chapman et al., Chem. Abstr., 101, 2173g, 1984.
Lanar et al., Biol. Abstr., 78, 67791, 1984.
Schechter et al., Infect. and Immun., 53, 547–552, Sep. 1986.
Snary et al., Biol. Abstr., 73, 61459, 1982.
Watson et al., Recombinant DNA, W. H. Freeman and Co., New York, 1983, pp. 86–87.

Primary Examiner—Robert J. Warden
Assistant Examiner—David A. Saunders
Attorney, Agent, or Firm—Townsend and Townsend

[57] ABSTRACT

T. Cruzi polypeptide antigens that react with serum from chagasic individuals and does not cross-react with serum from uninfected individuals or individuals infected with related parasites such as Leishmania is described. The DNA from T. Cruzi culture trypomastigotes and epimastigotes coding for antigenic material having a molecular weight of 70 kd is identified, sequenced, and inserted into a cloning vector, which, in turn, is inserted into a host cell line. The expressed polypeptide is immunologically reactive with sera from Chagas' disease infect patients. The cloned gene for the 70 kd polypeptide is expressed and purified and a diagnostic test for Chagas' disease comprising the synthesized polypeptide is described.

10 Claims, 9 Drawing Sheets

```
                    Oct 27 14:50 1986  70-47gene
                    Translation of clone pFP70-47

-----------------pUC9sequence-----------------
                   1                                            10
                   met thr met ile thr pro ser leu ala ala
TTTCACACAGGAAACAGCT ATG ACC ATG ATT ACG CCA AGC TTG GCT GCA ----------------] (T.cruzi DNA sequence------------> [--
                                    20
gly arg arg ile pro lys lys thr ala gly lys lys lys met
GGT CGA CGG ATC CCC AAA AAA ACA GCA GGA AAG AAG AAG AAA ATG ----remainder of DNA sequence is T.cruzi 70kd gene--------
            30                                          40
thr tyr glu gly ala ile gly ile asp leu gly thr thr tyr ser
ACG TAC GAG GGA GCC ATC GGC ATC GAT CTC GGC ACA ACT TAC TCG 50
cys val gly val trp gln asn glu arg val glu ile ile ala asn
TGC GTT GGT GTT TGG CAG AAC GAG CGC GTG GAG ATC ATT GCG AAC 60                                          70
asp gln gly asn arg thr thr pro ser tyr val ala phe thr asp
GAC CAG GGC AAC CGC ACA ACG CCG TCG TAC GTG GCG TTC ACC GAC 80
thr glu arg leu ile gly asp ala ala lys asn gln val ala met
ACG GAG CGT CTG ATC GGT GAT GCC GCG AAG AAC CAG GTT GCG ATG 90                                         100
asn pro thr asn thr val phe asp ala lys arg leu ile gly arg
AAC CCG ACG AAC ACC GTC TTC GAC GCG AAG CGC CTC ATT GGG CGG 110
lys phe ser asp pro val val gln ser asp met lys his trp pro
AAG TTC AGC GAC CCC GTT GTG CAG TCG GAC ATG AAG CAC TGG CCC 120                                         130
phe lys val ile thr lys gly asp asp lys pro val ile gln val
TTC AAG GTC ATC ACG AAG GGC GAC GAC AAG CCG GTG ATC CAG GTG 140
gln phe arg gly glu thr lys thr phe asn pro glu glu val ser
CAG TTC CGC GGC GAG ACA AAG ACG TTC AAC CCG GAG GAG GTG AGC 150                                         160
ser met val leu ser lys met lys glu ile ala glu ser tyr leu
TCG ATG GTG CTG TCA AAG ATG AAG GAG ATT GCG GAG TCG TAC CTG 170
gly lys gln val lys lys ala val val thr val pro ala tyr phe
GGC AAG CAG GTG AAG AAG GCC GTG GTG ACT GTG CCC GCG TAC TTC
```

FIG. 1
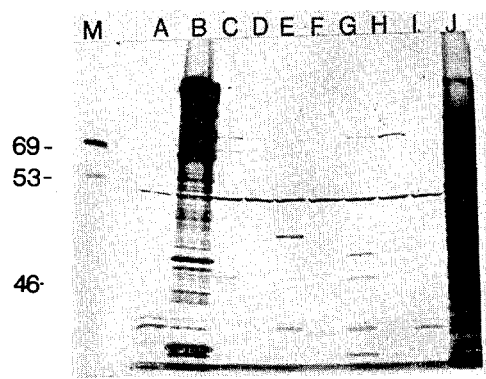
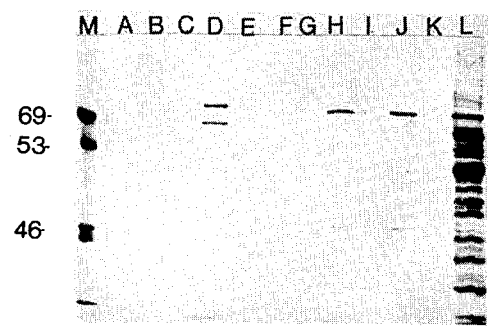
FIG. 2

FIG. 4-1

Oct 27 14:50 1986   70-47gene

Translation of clone pFP70-47

```
------------------pUC9sequence--------------------------
                  1                                   10
                  met thr met ile thr pro ser leu ala ala
TTTCACACAGGAAACAGCT ATG ACC ATG ATT ACG CCA AGC TTG GCT GCA ------------------] (T.cruzi DNA sequence--------------} [--
                                  20
gly arg arg ile pro lys lys thr ala gly lys lys lys lys met
GGT CGA CGG ATC CCC AAA AAA ACA GCA GGA AAG AAG AAG AAA ATG ----remainder of DNA sequence is T.cruzi 70kd gene---------
           30                                       40
thr tyr glu gly ala ile gly ile asp leu gly thr thr tyr ser
ACG TAC GAG GGA GCC ATC GGC ATC GAT CTC GGC ACA ACT TAC TCG 50
cys val gly val trp gln asn glu arg val glu ile ile ala asn
TGC GTT GGT GTT TGG CAG AAC GAG CGC GTG GAG ATC ATT GCG AAC -----------------------------------------------------------
           60                                       70
asp gln gly asn arg thr thr pro ser tyr val ala phe thr asp
GAC CAG GGC AAC CGC ACA ACG CCG TCG TAC GTG GCG TTC ACC GAC 80
thr glu arg leu ile gly asp ala ala lys asn gln val ala met
ACG GAG CGT CTG ATC GGT GAT GCC GCG AAG AAC CAG GTT GCG ATG 90                                      100
asn pro thr asn thr val phe asp ala lys arg leu ile gly arg
AAC CCG ACG AAC ACC GTC TTC GAC GCG AAG CGC CTC ATT GGG CGG 110
lys phe ser asp pro val val gln ser asp met lys his trp pro
AAG TTC AGC GAC CCC GTT GTG CAG TCG GAC ATG AAG CAC TGG CCC 120                                     130
phe lys val ile thr lys gly asp asp lys pro val ile gln val
TTC AAG GTC ATC ACG AAG GGC GAC GAC AAG CCG GTG ATC CAG GTG 140
gln phe arg gly glu thr lys thr phe asn pro glu glu val ser
CAG TTC CGC GGC GAG ACA AAG ACG TTC AAC CCG GAG GAG GTG AGC 150                                     160
ser met val leu ser lys met lys glu ile ala glu ser tyr leu
TCG ATG GTG CTG TCA AAG ATG AAG GAG ATT GCG GAG TCG TAC CTG 170
gly lys gln val lys lys ala val val thr val pro ala tyr phe
GGC AAG CAG GTG AAG AAG GCC GTG GTG ACT GTG CCC GCG TAC TTC
```

FIG. 4-2

Oct 27 14:50 1986  70-47gene

```
                    180                                              190
asn asp ser gln arg gln ala thr lys asp ala gly thr ile ala
AAC GAC TCC CAG CGG CAG GCG ACG AAG GAT GCC GGC ACG ATC GCG
                                        200
gly met glu val leu arg ile ile asn glu pro thr ala ala ala
GGG ATG GAG GTG CTG CGC ATC ATC AAT GAG CCG ACA GCT GCC GCC
                    210                                              220
ile ala tyr gly leu asp lys val glu asp gly lys glu arg asn
ATT GCG TAC GGC CTG GAC AAA GTG GAG GAC GGC AAG GAG CGC AAT
                                        230
val leu ile phe asp leu gly gly gly thr phe asp val thr leu
GTG CTC ATC TTT GAC CTT GGC GGC GGC ACG TTT GAT GTC ACG CTG
                    240                                              250
leu thr ile asp gly gly ile phe glu val lys ala thr asn gly
CTG ACG ATC GAC GGT GGC ATC TTT GAG GTG AAG GCG ACG AAC GGC
                                        260
asp thr his leu gly gly glu asp phe asp asn arg leu val ser
GAC ACG CAC CTG GGC GGC GAG GAC TTT GAC AAC CGC CTC GTG TCG
                    270                                              280
his phe thr asp glu phe lys arg lys asn lys gly lys asp leu
CAC TTC ACG GAC GAG TTC AAG CGC AAG AAC AAG GGC AAG GAC CTG
                                        290
thr thr ser gln arg ala leu arg arg leu arg thr ala cys glu
ACG ACA AGC CAG CGC GCC CTC CGC CGC CTC CGC ACC GCC TGC GAG
                    300                                              310
arg ala lys arg thr leu ser ser ala ala gln ala thr ile glu
CGC GCC AAG CGC ACG CTG TCG TCC GCG GCA CAG GCG ACG ATT GAG
                                        320
ile asp ala leu phe asp asn val asp phe gln ala thr ile thr
ATC GAC GCG CTG TTT GAC AAC GTG GAC TTC CAG GCA ACC ATC ACT
                    330                                              340
arg ala arg phe glu glu leu cys gly asp leu phe arg gly thr
CGC GCC CGC TTC GAG GAG CTC TGC GGC GAC CTC TTC CGA GGG ACG
                                        350
leu gln pro val glu arg val leu gln asp ala lys met asp lys
CTG CAG CCG GTG GAG CGT GTG CTC CAG GAC GCC AAG ATG GAC AAG
                    360                                              370
arg ala val his asp val val leu val gly gly ser thr arg ile
CGT GCC GTG CAC GAC GTG GTG CTC GTC GGC GGC TCC ACC CGC ATT
                                        380
pro lys val met gln leu val ser asp phe phe gly gly lys glu
CCA AAG GTG ATG CAG CTG GTG TCT GAC TTT TTC GGT GGC AAG GAA
```

FIG. 4-3

Oct 27 14:50 1986 70-47gene

```
                390                                                   400
leu asn lys ser ile asn pro asp glu ala val ala tyr gly ala
CTG AAC AAG AGC ATC AAC CCT GAT GAG GCT GTG GCG TAC GGT GCC 410
ala val gln ala phe ile leu thr gly gly lys ser lys gln thr
GCC GTG CAG GCC TTC ATC CTG ACG GGC GGC AAG AGC AAG CAG ACG 420                                                   430
glu gly leu leu leu asp val thr pro leu thr leu gly ile glu
GAG GGC CTG CTG CTC GAC GTG ACC CCG CTG ACG CTT GGC ATC GAG 440
thr ala gly gly val met thr ser leu ile lys arg asn thr thr
ACG GCG GGT GGC GTC ATG ACG TCG CTG ATC AAG CGC AAC ACG ACG 450                                                   460
ile pro thr lys lys ser gln ile phe ser thr tyr ala asp asn
ATT CCG ACC AAG AAA AGC CAG ATC TTC TCG ACG TAC GCG GAC AAC 470
gln pro gly val his ile gln val phe glu gly glu arg ala met
CAG CCG GGC GTG CAC ATC CAG GTC TTT GAG GGG GAG CGT GCG ATG 480                                                   490
thr lys asp cys his leu leu gly thr phe asp leu ser gly ile
ACG AAG GAC TGC CAC CTG CTC GGC ACA TTC GAC CTG TCC GGC ATC 500
pro pro ala pro arg gly val pro gln ile glu val thr phe asp
CCG CCG GCG CCG CGC GGT GTG CCC CAG ATT GAG GTT ACC TTT GAC 510                                                   520
leu asp ala asn gly ile leu asn val ser ala glu glu lys gly
CTC GAC GCC AAC GGC ATC CTG AAC GTG TCC GCG GAG GAG AAG GGC 530
thr gly lys arg asn gln ile val ile thr asn asp lys gly arg
ACC GGC AAG CGC AAC CAG ATT GTC ATC ACG AAC GAC AAG GGC CGC 540                                                   550
leu ser lys ala asp ile glu arg met val ser glu ala ala lys
CTG AGC AAG GCG GAC ATT GAG CGC ATG GTG TCC GAG GCT GCC AAG 560
tyr glu ser gln asp lys glu gln arg glu arg ile asp ala lys
TAC GAG TCG CAG GAC AAG GAA CAG CGC GAG CGC ATT GAC GCA AAG 570                                                   580
asn gly leu glu asn tyr ala phe ser val lys asn thr val asn
AAC GGT CTT GAG AAC TAC GCA TTT TCG GTG AAG AAC ACC GTA AAC 590
glu pro asn val ala gly lys ile glu glu ala asp lys asn thr
GAG CCG AAC GTC GCT GGC AAG ATT GAG GAG GCC GAC AAG AAC ACG
```

FIG. 4-4

Oct 27 14:50 1986 70-47gene

```
              600                                                           610
ile thr ser ala val glu glu ala leu gln trp leu asn asn asn
ATT ACG AGT GCC GTG GAG GAG GCG CTG CAA TGG CTG AAC AAC AAC 620
gln glu ala ser lys glu glu tyr glu his arg gln lys glu leu
CAG GAG GCC AGC AAG GAG GAG TAC GAG CAC CGC CAG AAG GAG CTG 630                                                           640
glu asn leu cys thr pro ile met thr lys met tyr gln gly met
GAG AAC CTG TGC ACG CCC ATC ATG ACG AAG ATG TAC CAG GGC ATG 650
gly ala gly gly gly met pro gly gly met pro gly gly met pro
GGC GCG GGC GGC GGT ATG CCC GGA GGT ATG CCT GGT GGA ATG CCC 660                                                           670
gly gly met pro gly gly ala asn pro ser ser ser ser gly pro
GGG GGC ATG CCT GGT GGC GCG AAC CCG TCG TCT TCG TCA GGA CCG 676
lys val glu glu val asp OP
AAG GTG GAG GAA GTG GAC TGA GAGCGCATCCCTGAAGATGTTCCCATGGCGGCG
```

TCTGCTCGCGAACGAATAACCCGTTGGTTTTCTCCCTTGTAGAGCGTAGAGGTCTGCGAC

AAACCCAGCCGCCATCACTATTTTTATTATTGGTTTTTTTCCCTCTCCATTATTATTATT

ATTATTATTATTATTACGGTTGTTATTTGTATTGTCATTGCGATGGCACTTGTGCTG

TTGAGGGCACCACGGTTGCCTCTGCCATTTTTGTTGCTGACTGACGCCTGTGTGCGTCTC

CTTGTACCGCCGGCTTCCTTTCCTCCTTTCTCCCCCGCTCCTTCGCCCTGTGCCACGGAG

CACGCCAGAATCAATCAAGGTCGAGAGTTAACTTT

Translated Mol. Weight = 73748.90

ANTIGENIC MATERIAL FOR A CHAGAS' DISEASE DETECTION SYSTEM

This invention was made with government support under Contract No. 5R44AI20839-03 awarded by the National Institutes of Health. The government has certain rights in the invention.

This is a continuation-in-part of Ser. No. 889,419, filed 7/24/86.

FIELD OF THE INVENTION

This is a continuation-in-part application of United States Ser. No. 881,419.

This invention relates to an antigenic material useful for the diagnosis of Chagas' disease, and more particularly to a polypeptide synthesized using genetic engineering techniques useful for the detection of Chagas' disease, the process for producing the same, the constructs for said process, and a system for detecting Chagas' disease employing said polypeptide.

BACKGROUND AND PRIOR ART

*Trypanosoma cruzi*, (*T. cruzi*) a hemoflagellate, is the causative agent of Chagas' disease. Chagas' disease is a major health problem in Central and South America, especially Mexico, Brazil, Chile and Argentina. It is currently estimated that at least 12 million individuals are infected with the protozoan parasite (Hudson, 1981). In addition, there have been occassional reports of occurrence of Chagas' disease in California and Texas.

Chagas' disease principally occurs in rural areas and correlates with poor housing and sanitary conditions. Houses are excellent breeding places for the insect vector, a common blood sucking parasite (reduviid sps. *Triatoma, Panstrongylus* and/or *Rhodnius*), which transmits the disease between vertebrate hosts, such as man, domestic pets including cats and dogs, and wild mammals.

When an insect host, containing infectious metacyclic trypomastigotes in its hindgut, defecates onto the skin of its victim while feeding and engorging on the victim's blood, the *T. cruzi* trypomastigotes are deposited on the victim. These trypomastigotes can then easily penetrate the mucosae once the skin has been broken by wound, abrasion, etc. The simple act of scratching the bite area facilities entry of the parasite into the victim.

*T. cruzi* exists in a number of different morphological forms. Epimastigotes and metacyclic trypomastigotes are normally found in the insect midgut and hindgut, respectively. Blood form trypomastigotes are found in the circulation of infected vertebrates. The amastigote lives and reproduces inside vertebrate host cells. Epimastgotes have been the normal source of diagnostic antigens since they can be grown cheaply in axenic culture. Although it is believed that the trypomastigotes would be a superior source of antigens, their high cost of production and the higher risk of infection has generally precluded their use.

The progression of Chagas' disease is divided into two phases. In the initial acute phase there is a parasitemia present accompanied by mild flu-like symptoms or no apparent symptoms at all. After approximately two weeks the host's immune system clears the circulating parasites and the chronic phase is established. During the chronic phase the parasites exist intracellularly thereby escaping immune surveillance. After several years the symptoms of the chronic phase of Chagas' disease may appear, including myocardia enlargement, hardening of the esophagus and/or lower intestine, and neuromotor problems. Autoantibodies to neural and muscular antigens are usually associated with the chronic form of Chagas' disease. Chagas' disease is especially insidious because there are no satisfactory prophylactic or curative agents available and because an individual, once he has contracted the disease, remains infected for life.

The only useful diagnostic parameters during the final stage of the disease are either parasitological or immunological testing, due to the variability or possible lack of specific clinical symptoms. Parasitological diagnosis during the chronic phase is expensive, time-consuming and often extremely distasteful to the patient. Because circulating parasites cannot be detected by direct examination of blood smears, parasitological testing (xenodiagnosis) must be employed. In such tests, reduviid bugs are permitted to feed on the patient, and the hindguts of the reduviid bugs are examined under microscope 30 days after such feeding to determine if *T. cruzi* is present.

The preferred and more widely used tests for Chagas' disease detection are immunological (serological) analysis, including immunofluoresence (IF); complement fixation (CF); either direct (DA) or indirect hemagglutination (IHA); latex agglutination (LA) and enzyme-linked immunoassay (ELISA).

However, the current serological tests are unsatisfactory for a number of reasons. First, a large variation exists between these tests; for example, a serum giving a high titer from one test frequently gives a low or moderate titer in another test. Due to this variation, three different serological tests must generally be performed in parallel and at least two of them must give high titers for positive diagnosis. Second, production of the diagnostic reagents is hazardous because the parasites must be grown and handled to produce the antigen extracts. Third, use of crude mixed antigen preparations (basically fixed epimastigotes) causes cross-reactivity with patients who have Leishmania (another endemic parasitic protozoan), so that many false positives are indicated. Fourth, at least some of the other test methods require the use of sophisticated laboratory equipment not generally available or practical in the geographic areas with a high incidence of Chagas' disease.

The development of a sensitive and accurate diagnostic test for Chagas' disease has a high priority, particularly in Central and South America, where over 200 million individuals are at risk of infection. To facilitate this goal it is necessary to identify and isolate unique *T. cruzi* proteins which are specifically recognized by the serum from chagasic patients.

The literature on *T. cruzi* contains conflicting data concerning immunoreactive surface proteins and glycoproteins. Many researchers have described glycoproteins in the 70 kd 95 kd region, yet it is not clear which specific proteins the different reports are describing. The cell surface components of several morphological forms of *T. cruzi* have been radiolabeled and analyzed by one and/or two-dimensional polyacrylamide gel electrophoresis (1D- or 2D-PAGE). A 72 kd surface protein has been identified on epimastigotes and metacyclic trypomastigotes [Snary and Hudson, (1979); Nogueira et, al, (1981); Snary et al, (1981); Zingales et al, (1982); and Lanar and Manning, (1984)). A 90 kd surface protein has been identified in bloodstream and tissue culture-derived trypomastigotes Snary and Hudson, (1979); Araujo and Remington, (1981); Nogueira et al, (1981); Snary et al, (1981); Zingales et al, (1982); Nogueira et al, (1982); and Lanar and Manning, (1984)]. In addition, Snary and Hudson, (1979) and Zingales et al, (1982) have reported the 90 kd protein on epimastigotes, although Nogueira et al, (1982); Manning (1984) and Dragon et al, (1985) have not seen this. Katzin and Colli (1983) have identified an 85 kd trypomastigote specific protein. Lanar and Manning (1984) have determined with radioimunoassays and western blot analysis that the 90 kd protein is one of the major antigenic components recognized by sera from mice chronically infected with T. cruzi. Nogueira et al have shown that IgG isolated from the blood of 5 patients hospitalized in Brazil with chronic Chagas' cardiopathy primarily reacts with proteins in the 90 kd region. Further, a 25 kd protein has also been reported as being cross-reactive with chagasic sera [Scharfstein et al, (1983)].

Thus, there is a need for a detection system for Chagas' disease which provides reproduceable results, and which is relatively easy, safe and inexpensive to manufacture and perform. Recombinant DNA technology is available to accomplish the foregoing objectives.

SUMMARY OF THE PRESENT INVENTION

Complementary DNA (cDNA) libraries to both epimastigote and tryposmatigote A+ RNA of T. cruzi were constructed and screened by hybrid-selection/-translation. From an epimastigote cDNA library cloned into pUC 18, 96 random cDNA clones were selected and inoculated into individual wells of a microtiter dish. Mixed plasmid preps were prepared from pools of 12 clones. The DNA was purified, linearized, and immobilized onto nitrocellulose filters. Hybrid-selection/translation experiments were performed using epimastigote total RNA. Several specific polypeptides were recognized by the chagasic sera including an 85 kd, 70 kd and 40 kd polypeptide and the hybridizing clones for these polypeptides were selected for isolation and cloning. The cDNA clones coding for the selected polypeptides were identified, isolated and characterized. Specific oligonucleotide probes were designed and prepared from the sequences of the selected cDNAs. A "Sau3A partial" epimastigote genomic DNA library was constructed in the lambda phage EMBL3 and inserted into an E. coli host. Using the above oligonucleotide probes, clones were isolated from the library corresponding to each of the cDNAs.

The gene structure for the synthesized 70 kd polypeptide has been determined. A cloning vector has been prepared including the gene encoding the 70 kd polypeptide. An E. coli containing the prepared vector has been made and employed in the synthesis of the 70 kd polypeptide. Derivatives of the 70 kd polypeptide may also be employed. The expressed polypeptide is rendered antigenically active by denaturation and renaturion as described in McCaman et al (1985).

From the 70 kd polypeptide, a diagnostic reagent for Chagas' disease can be made which is less expensive, safer and more specific than any of the diagnostic reagents currently available. The 70 kd polypeptide is recognized by all of the chagasic sera tested (2 Argentinian, 1 Columbian, and 1 1 Brazilian), but not by Leishmania sera.

BRIEF DESCRIPTION OF THE DRAWINGS

FIG. 1 is fluorogram of a 10% SDS-polyacrylamide gel of a hybridization-selection/translation (HST) experiment using mixed plasmid pools of DNA. Lane M contains the Molecular Weight Standards, Lanes A through I contain the translation products of: Lane A - RNA control, Lane B - BMV mRNA control, Lane C - Pool C DNA, Lane D - Pool D DNA, Lane E - Pool E DNA, Lane F - Pool F DNA, Lane G - Pool G DNA, Lane H - Pool H DNA, Lane I pUC9 DNA. Lane J contains the translation products of epimastigote total RNA.

FIG. 2 is a fluorogram of a 10% SDS-polyacrylamide gel of the immunoprecipitation products of the experiment described above in reference to FIG. 1. Lane M contains the Molecular Weight Standards, Lane A contains the polypeptides from pUC9 (HST) immunoprecipitated with normal human sera (NHS), Lane B contains the polypeptides from pUC9 (HST) immunoprecipitated with chagasic sera (CHA), Lane C contains Pool C (HST) immunoprecipitated with NHS, Lane D contains Pool C (HST) immunoprecipitated with CHA, Lane E-Pool E (HST) immunoprecipitated with NHS, Lane F-Pool E immunoprecipitated with CHA, Lane G-Pool G (HST) immunoprecipitated with NHS, Lane H-Pool G (HST) immunoprecipitated with CHA, Lane I-Pool H immunoprecipitated with NHS, Lane J-Pool H (HST) immunoprecipitated with CHA, Lane K-total translated epimastigote RNA immunoprecipitated with NHS, Lane L-total translated epimastigote RNA immunoprecipitated with CHA.

FIGS. 4-1 through 4-4 show the complete DNA sequence of the gene for the 70 kd polypeptide. The putative amino acid sequence of the open reading frame is shown above the corresponding DNA sequence. The cDNA clone corresponding to this gene is also indicated on this sequence. The sequence was determined by the methods described in Sanger (1975), Sanger (1977) and Henikoff (1984). Nucleotide 1 refers to the A (adenosine) of the potative initiator ATG codon. The designation "-" numbers refer to bases upstream of the first ATG.

DETAILED DESCRIPTION OF THE PREFERRED EMBODIMENT

Figure 3:
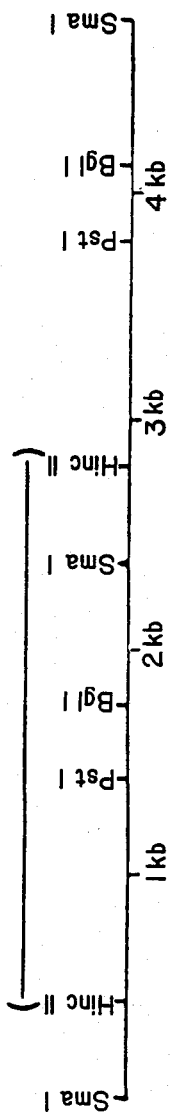
FIG. 3 is a restriction map of two tandemly linked 2.4 kb SmaI inserts (i.e. 2 copies of the pEG22 insert). The dark line above the map indicates the domain of the transcript the 70 kd polypeptide
Figure 5:
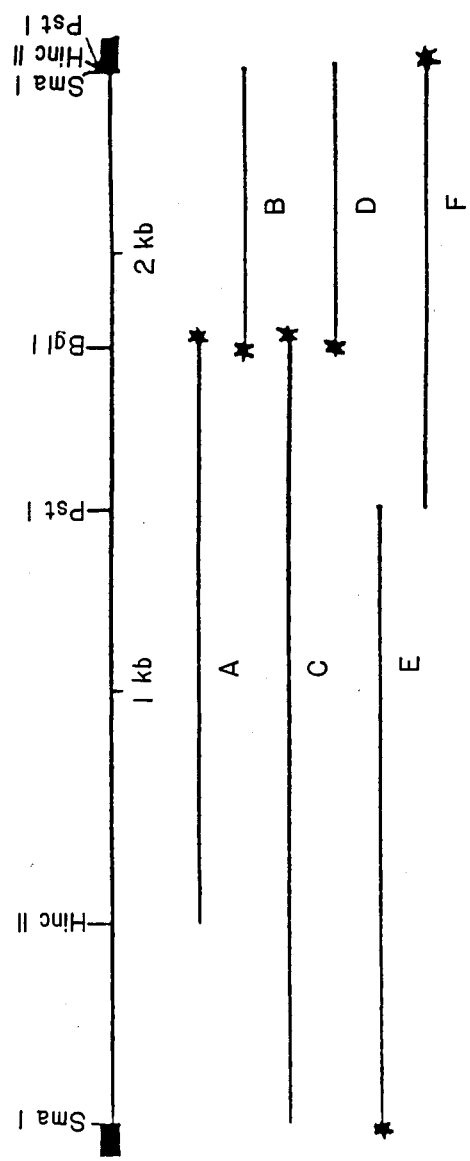
FIG. 5 illustrates which fragments were used for S1 analysis of the 70 kd polypeptide: Fragment A is a 1318 bp BglII/Hinc II fragment, Fragment B is a 627 bp BGlII/HincII fragment, Fragment C is a 1751 bp fragment and Fragment D is a 609 bp BglII/SmaI fragment. Fragments A, B, C and D are 5' end labelled at the BglII site. Fragments E and F are, respectively, 1417 bp and 943 bp XmaI/PstI fragments, 5' end labelled at the XmaI site.
Figure 6:
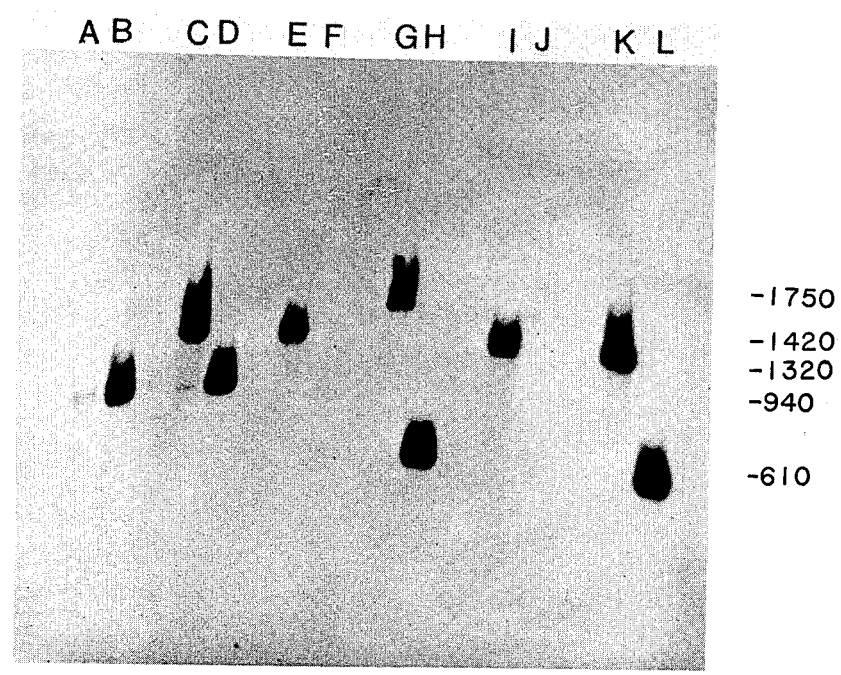
FIG. 6 shows an autoradiogram of an alkaline agarose gel analysis of the S1 nuclease mapping of the 70 kd polypeptide transcript. Lane A is the S1 treated Fragment E, Lane B is the S1 treated Fragment F, Lane C is untreated Fragment E, Lane D is untreated Fragment F, Lane E is S1 treated Fragment C, Lane F is the S1 treated Fragment D, Lane I is S1 treated Fragment A, Lane J is S1 treated Fragement B, Lane K is untreated Fragment A and Lane L in untreated Fragment B. The results of this experiment demonstrates that, as expected, the non-complementary Fragments B, D, and E were not protected by RNA and therefore were degraded. Both Fragments A and F were completely protected by RNA, demonstrating that there are no introns between the HincII site at −36 and the SmaI site at 1891 (numbering refering to the gene sequence in FIG. 4). Fragment C was reduced in size by approximately 430 bp. indicating that the start of the transcript is very close to the HincII site at −36.
Figure 7:
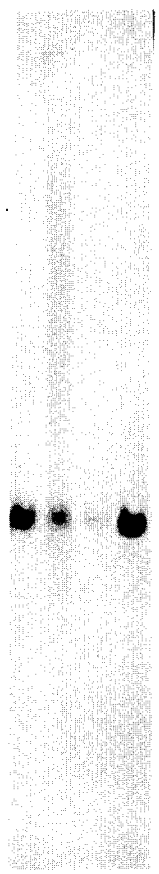
FIG. 7 is a autoradiogram of an Northern Blot analysis of RNA coding for the 70 kd antigen showing the size of the mRNA homologous to a genomic subclone hybrid-selecting the 70 kd antigen. RNA was fractionated by electrophoresis in a 1% agarose gel containing formaldehyde, and subsequently blotted onto nylon. Lanes A and B are 10 ug of two different total epimastigote RNA preparations. Lane C is 0.5 ug of trypomastigote A+mRNA. Lane D is 1 ug of epimastigote A+mRNA. Lane D is 1 ug of epimastigote A+mRNA. The hybridization probe was a nick-translated 1900 bp HincII fragment from pEG22.

Two important features for a diagnostic antigen for Chagas' disease are that the antigen must be reactive with serum isolated from people living in distict geographic locations and that the antigen should not be reative with sera from Leishmania infected patients. Approximately 30 different chagasic sera from different countries in North and South America have been obtained. (Brazil, Mexico, Venezuela and Argentina). Six sera positive for Leishmaniasis (5 Panamanian, *L. brasiliensis*, and 1 Mexican, *L. Mexicana*) have also been obtained to be used in testing the Chagas' antigen for lack of cross-reactivity with *Leishmania* antisera. The Peru strain of *T. cruzi* was chosen since it is highly virulent and large amounts may be isolated from infected tissue culture or mice.

Growth and Isolation of Parasites

*Trypanosoma cruzi*, Peru strain, was used in all experiments. Epimastigotes were grown at 28° C. in modified HM (Warren, 1960): 37 g/l brain heart infusion (Difco Lab., Detroit, Mich.), 2.5 mg/l hemin, 10% heat-inactivated fetal calf serum. Log phase cells were harvested by centrifugation and washed twice with cold PSG (20 mM sodium phosphate, pH 7.4, 0.9% NaCl, 1.0% glucose). Culture form trypomastigotes were obtained from infected Va-13 cells as previously described [Sanderson et al, (1980); Lanar and Manning, (1984)].

Isolation of DNA and RNA

Parasites were harvested from culture by centrifugation and washed several times with PSG (20 mM sodium phosphate, pH 7.4, 0.9% NaCl, 1.0% glucose). Epimastigotes were resuspended at a concentration of $10^9$ /ml in PEG/EGTA buffer (20 mM Tris-HCl, pH 7.6, 25 mM EGTA, 50 mM MgCl, 25 mM CaCl, 1.0% Triton-X100, and 4 mM dithiothreitol), plus 250 u/ml of RNASin (Promega Biotec, Madison, Wis.), incubated on ice for 20 min, centrifuged at 8000×g for 15 minutes at 4° C. The supernatant containing the RNA was phenol extracted 3 times, then extracted once with chloroformisoamyl alcohol (24:1) and ethanol precipitated. The pellet (nuclei and kinetoplasts) was resuspended at a concentration of $10^9$ parasite equivalents/ ml in 10 mM Tris-HCl, pH 8.0, 50 mM EDTA, 0.1% SDS, 150 ug/ ml Proteinase K (Boehringer-Mannheim, Indianapolis, Ind.) and incubated at 65° C. for 1 hour. After cooling to room temperature, the DNA was gently extracted with an equal volume of phenol for 1 hour. This extraction was repeated once, and the aqueous phase was extracted with chloroform-isoamyl alcohol (24:1) once. The DNA was recovered by ethanol precipitation The DNA pellet was gently redissolved in 10 mM Tris-HCl, pH8.0, 1 mM EDTA and treated with 0.15 mg/ml DNAse-free RNAseA for 30 minutes at room temperature. After RNAse digestion the sample was extracted once with phenol, once with chloformisoamyl alcohol and then precipitated with ethanol. The size of the DNA was determined to be greated than 20 kilobase pairs (kb) on agarose gels. Trypomastigote DNA and RNA was prepared in an identical manner except that the parasites were resuspended at a concentration of $5\times 10^9$/ml.

Preparation of A+mRNA

Poly A+containing RNA was isolated by oligo(dT)-cellulose chromatography (Aviv and Leder, 1972). Total RNA was loaded onto an oligo(dT)-cellulose column (Type 3, Collaborative Research, Lexington, Mass.) in 10 mM Tris-HCl, pH 7.5, 1 mM EDTA, 0.2% SDS, 400 mM LiCl. RNA was eluted from the column at 40° C. with 10 mM Tris-HCl, pH 7.5, 1 mM EDTA, 0.2% SDS.

Construction of the *T. cruzi* "Sau3a Partial" Genomic Library in Bacteriophage EMBL3

200 ug of *T. cruzi* epimastigote DNA was digested with the restriction endonuclease Sau3A (Boehringer-Mannheim, Indianapolis, Ind.) according to manufacturer's specifications. Aliquots of the reaction were removed at 1, 2.5, 5, 10, 20, 40 and 60 minutes. Upon removal each aliquot was diluted to 25 mM in EDTA and heated for 15 minutes at 68° C. The samples were pooled, the DNA was size fractionated over a Sephacryl S-1000 column (Pharmacia, Piscataway, N.J.) in 200 mM Tris-HCl, pH7.5, 100 mM NaCl, 1 mM EDTA. Those fractions containing DNA in size from 5 kb to 20 kd were pooled ethanol precipiated and used for cloning. The lambda bacteriophage cloning vector EMBL3 (Frishauf et al, 1983) was used. EMBL3 arms and GIGAPAK packaging system were purchased from Vector Cloning Systems (San Diego, Calif.) and used according to the manufacturer's instructions.

Hybridization-Selection/Translation

Specific *T. cruzi* RNAs were purified from total *T. cruzi* RNA using the technique of hybridization-selection/translation as described by Riccardi et al, 1972. 25–50 ug of purified plasmid DNA was digested with an appropriate restriction endonuclease (to linearize the plasmid), the DNA was cleaned by phenol extraction and chloroform extraction and denatured by boiling for 10 minutes. Following boiling, the DNA was quick-frozen, thawed, then spotted onto a 9 mm diameter nitrocelulose filter. The filter was washed several times with 6XSSC, then air dried and baked for 2 hours at 80° C. in vacuo. For hybridization, 100 ug of *T. cruzi* total RNA was reacted with the DNA containing filter in a solution containing 65% formamide, 0.01 M PIPES, pH 6.4, 0.4 M NaCl at 65° C. for 3 hours. Following the hybridization reaction, the filter is washed 10 times with 1XSSC, 0.1% SDS at 60° C., 3 times with 0.002 M EDTA at 60° C. and once with water at room temperature. The specifically hybridized mRNA is eluted from the filter by boiling the filter in a small volume of water for two minutes, quick-freezing the solution, then ethanol precipitation of the RNA. The purified RNA is resuspended in water, then translated in an in vitro translation system (such as rabbit reticulocyte).

Immunoprecipitation Reactions

A 1:10 to 1:50 dilution of individual serum was prepared using 10 mM Tris-HCl, pH7.5, 1% Nonidet P-40 (NP-40), 1 mM N-alpha-p-tosyl-L-lysine chloromethyl ketone (TLCK), 1 mM phenyl methyl sulfonyl fluoride (PMSF), and 2.8 Kallikrein Inactivator Units (KIU)/ml aprotinin. The diluted serum was mixed with an equal volume of cell-free translation reaction mixture, and incubated overnite at 4° C. 10 ul of a 10% Protein-(Pharmacia, Piscataway, N.J.) was added and gently mixed for 1 hour at 4° C. The immune complexes were washed and analyzed on SDS-polyacrylamide gels as described in Dragon et al, 1985.

Synthesis of cDNA cDNA was synthesized by methods known to those of ordinary skill in the art. Briefly, 2 ug of epimastigote or trypomastigote A+mRNA was transcribed by the action of AMV reverse transcriptase as described by Ullrich et al, 1977. Transcription was initiated at the 3′ polyadenylated end of the mRNA using oligo(dt) as a primer. The second strand was copied using DNA polymerssel and RNAseH (Boehringer-Mannheim, Indianapolis, Ind.) and appropriate buffers (Gubler, 1983).

Specifically, 2 micrograms of oligo-dT (12-18 nucleotides, Pharmacia Molecular Biology Division, Piscataway, N.J.) was annealed to 2 micrograms of purified mRNA in the presence of 50 mM NaCl. The annealing reaction was heated to 90° C. and then slowly cooled. For the reverse transcripcase reaction, deoxynucleosidetriphosphates (dATP, dTTP, dGTP and dCTP) were added to make a final concentration of 0.5 mM, along with 40 units of enzyme (Molecular Genetic Resources, Tampa, Fla.). The reverse transcriptase reaction buffer contained 15 mM Tris-HCl, pH 8.3, 21 mM KCl, 8 mM MgCl$_2$, 0.1 mM EDTA, and 30 mM beta-mercaptoethanol. This mixture was incubated at 42° C. for 45 minutes. The RNA-DNA duplex was extracted once with phenol chloroform and then precipitated with ethanol. The pelleted material was then resuspended in 100 microliter reaction mixture containing the following: 20 mM Tris-HCl pH 7.5, 5 mM MgCl$_2$, 100 mM KCl and 250 uM each dATP, dCTP, dTTP, dGTP.

RNAase H (100 units/ml Pharmacia Molecular Biology Division, Piscataway, N.J.) and DNA Polymerase I —Klenow fragment (50 units/ml Boehringer Mannheim, Indianapolis Ind.) were added and the reaction was incubated at 12° C. for 60 minutes. The combined activities of these enzymes result in the displacement of the RNA from the RNA-DNA duplex as the first cDNA strand is used as a template for synthesis of the second cDNA strand. The reaction was stopped by the addition of EDTA to a final concentraction of 10 mM and the DNA duplex was then extracted with phenol: chloroform and ethanol precipitated. The sequence of the reactions of DNA Polymerase I and RNAase H was predicted to yield cDNA molecules which were blunt ended at both their 3′ and 5′ ends. A 3′ blunt end is necessary for the subsequent cloning of the cDNA.

Construction of the cDNA Library

Briefly, the double stranded cDNA preparations were digested with the restriction endonuclease SacI and PvuII (New England Biolabs, Beverly, Mass.) and ligated, using T4 DNA ligase, into the SacI and SmaI sites of the plasmid pUC18 (Yanish-Perron et al, 1985). This mixture was used to transform E. coli K12 strain JM83, selecting for ampicillin resistance conferred by the introduction of the pUC18 into the host cell. From 2 ug of mRNA approximately 150 ng of cDNA were prepared which yielded about 7000 ampicillin resistant recombinant clones.

More specifically, the cDNA was resuspended in 100 microliters of sterile water. Approximately 50 ng was digested with SacI (5000 units/ml) and PVUII (12000 units/ml) in the presence of 6 mM Tris-HCl (pH 7.4) 6 mM MgCl$_2$, and 6 mM beta-mercaptoethanol for 60 minutes at 37° C.

The sample was then re-extracted with phenol:-chloroform and ethanol precipitated. For the cloning step a pUC 18 vector (32) was used. The vector had been digested with SacI and SmaI. SmaI provided the blunt end site necessary for ligation of the 3′ end of the cDNA. The ligation reaction was performed using 40 ng of vector DNA and 50 ng of cDNA. Ligations were done overnight at 12° C. in a ligase buffer of 50 mM Tris-HCl (pH 7.8), 10 mM MgCl$_2$, 20 mM dithiothreitol, 1.0 mM rATP using one unit of T4 DNA ligase.

The recombinant DNA molecules were then introduced into E. coli K-12 strain JM83 by transformation. The transformed bacteria were spread on agar plates containing the antibiotic ampicillin at a concentration of 50 micrograms/ml. Since the plasmid pUCl 8 (32) contains the ampicillin resistance gene, only those bacteria which acquired a recombinant plasmid survived. These bacteria each grew and divided to form a bacterial colony. Each cell in the colony is a descendant of the original parental cell and contains the same recombinant plasmid. Using hybridization selection/translation and immunoprecipitation techniques to screen the cDNA library a clone was identified which contained nucleotide sequences corresponding to a 70 kd T. cruzi peptide.

Isolation of the full length 70 kd gene

The cDNA clone was used as a probe to screen the T cruzi Sau3a partial genomic library as described by Maniatis et al. In this manner a full length copy of the 70 kd gene was obtained. This clone, FG21, was sequenced and used to construct an expression plasmid to allow production of the 70 kd antigen in E. coli.

Expression of Cloned Genes in E. coli

Several systems are available in the laboratory for expressions of foreign genes in E. coli and other mammalian and bacterial tissue culture cell lines. It is important to provide the cloned gene with an E. coli ribosome binding site for initiation of translation and a strong promotor to obtain sufficiently high levels of protein. Although obtaining "direct" expression of the protein is possible, it appears to be more efficient to produce the protein as a fusion protein the amino terminus of which is a small part of an E. coli protein containing signals for the initiation of protein synthesis. The amino terminus of B-lactamase and the amino terminus of B-galactosidase toridase as well as the lamb and the calf chymosin gene can make such fusion proteins [Hegpeth et al., (1980), Lingappa et. al., (1984)]. These and other systems may be used to obtain expression of the cloned gene.

Sequencing analysis showed that the coding region of the 70 kd gene was flanked by an AhaIII site 30 base pairs upstream from the putative ATG start codon. An additional AhaIII site is located 367 base pairs following the TGA stop codon in the nucleotide sequence of FG21. Subsequently FG21 was digested with the restriction enzyme AhaIII. The resulting DNA fragment was 2,341 base pairs long. It was gel purified and cloned into the SmaI site of the expression vector pUC9. The resulting plasmid, pFP70-47, was used to transform E. coli K12 SG936 bacteria. A sample of this recombinant bacteria has been placed on deposit with with the American Type Culture Collection as ATCC number 67254 strain, SG936/FP70-47 produces a 70 kd polypeptide which can react with chagasic sera.

Since polyclonal antisera recognize a variety of antigenic determinants on a protein molecule, it may only be necessary to clone and express a fragment of the 70 kd polypeptide gene. Expression of the entire protein, however, provides as many determinants as possible on the target antigen.

Antigen Production

The transformed E. coli are grown in liquid culture containing 50 micrograms per ml. of ampicillin to enhance plasmid ability. Cultures are harvested at an OD of 2.0 measured at 550 nm. The cells are then pelleted, washed and lysed by freeze/thaw and sonication. A detergent extraction solubilizes most of the remaining polypeptides. The 70 kd expressed product, however, remains insoluble and is harvested by centrifugation. This insoluble "cement" is denatured in urea and subsequently diluted at a high pH and the pH is then adjusted back to neutral. During the renaturation process the antigen refolds and achieves that immunologically active conformation. The details of this procedure used are identical to those used to restore enyzme activity to recombinant chymosin as described by McCaman el al (1985).

Diagnostic System Kit

Two types of diagnostics for Chagas' disease to measure antibody level in individuals are preferred namely, (1) an ELISA for sensitive testing and (2) a latex agglutination test for "field" test. An ELISA appears to be the method of choice for high sensitivity for specific serodiagnosis of Chagas' disease [(Voller et. al., (1975); Spencer et. al, (1980); Anthony et al., 1979; Schechter et. al, (1983)]. In an ELISA test system for Chagas' disease, plastic microtiter dishes are coated with different concentrations of antigen, washed, and various dilutions of sera will be added to each well. The plates are incubated at room temperature, washed several times, then the appropriate anti-human globulin serum conjugated with either horseradish peroxidase or alkaline phosphatase will be added and incubated for an appropriate period of time at room temperature. The plates are washed several times, then the appropriate substrate is added and the color reaction proceeds. Intensity of color development can be assessed visually or with a spectrophotometer. Alternatively, "dot blots" can be performed to to screen sera [Pappas et. al., (1983)]. The results of this series of assays provides the optimal as well as minimal levels of sensitivity using the synthesized 70 kd antigen.

Enders et al, (1975) reported success using a latex agglutination test for the serodiagnosis of Chagas' disease. This test is very easy to perform, quick, and requires very little special equipment or reagents. A solution of the appropriate antigen is adsorbed onto latex beads. One drop of serum is mixed with one drop of the latex reagent on a black glass plate, the plate is gently rocked for 5 to 10 minutes and the result can be read as a flocculation of the suspension. A Chagas' negative serum leaves a homogeneous suspension. One particular advantage of this test is that there is no decrease in sensitivity or specificity of the reagent if stored at or below 20° C.

It will be obvious to a person of ordinary skill in the art, that the present invention encompasses many different embodiments not specifically addressed herein. For example, minor modifications may be made to the genetic material encoding the 70 kd antigen by way of interchanging individual amino acids such that the codons code for the same amino acid sequence as . described herein. The present invention also includes modifications which may be made to the amino acids sequence disclosed including the utilization of polypeptides comprising only a portion of the complete 70 kd polypeptide and having immunological cross-reactivity with chagasic sera. Chemically modified polypeptides of the type described above are also contemplated Any of the foregoing modifications are referred to herein as "derivatives." Therefore, the present invention is not to be construed to be limited by the embodiments specifically recited, rather it is intended to include all subject matter covered by the appended claims, and equivalents thereof.

References

1. Anthony, R. L., C. M. Johnson and O. E. Sowa (1979) Am J. Trop. Med. Hyg. 28, 969–973.
2. Araujo, F. G. and J. S. Remington (1981), J. Immunology 127, 855–859.
3. Aviv, H. and Leder P. (1972) Proc. Nat. Acad. Sci. USA 69, 1408–1412.
4. Beard, Chris A., Wrightsman, Ruth A., and Manning, Jerry E. (1985) Molecular and Biochemical Parasitology 16, 199–212.
5. Dragon, E. A., Brothers, V. M., Wrightsman, R. A. and Manning, J. E. (1985) Molecular and Biochemical Parasitology 16, 213–229.
6. Enders, B., K. D. Hungener and O. Zwisler (1975) Tropenmed. Parasit. 26, 252–260.
7. Frischauf, A-M, Lehrach, H., Poustks, A., and Murray, N. (1983) J. Mol. Biol. 170, 827–842.
8. Gubler, U. and Hoffman, B. J. (1983) Gene 25, 263–269.
9. Hedgpeth, J., M. Ballivet and H. Eisen (1978) Mol. Gen. Genet. 163, 197–203.
10. Henikoff, S. (1984) Gene 28, 351–359.
11. Lingappa, V., J. Chaidez, C. S. Yost and J. Hedgpeth (1984) Proc. Nat. Acad. Sci. USA 81, 456–460.
12. Katzin, A. M., and W. Colli (1983) Bio. Biophy. Acta. 727, 403–411.
13. Lanar, D. E. and Manning, J. E. (1984) Molecular and Biochemical Parasitology 11, 119–131.
14. Maniatis, R., Fritsch, E. F., and Sambrook, J. Cold Spring Harbor Laboratories, Cold Spring Harbor, N.Y., 1982.

5. McCaman, M., Files, J., and Andrews, B., Journal of Biotechnology vol 2 1985 117-191.
16. Morrow, R. H. (ed) (1983) TDR/EPI/Diag. Methods/1982, World Health Organization.
17. Nogueira, J. Unkeless and Z. Cohn (1982) Proc. Nat. Acad. Sci. 79, 1259-1263.
18. Nogueira, N. S. Chaplan, J. D. Tydings, J. Unkeless and Z. Cohn (1981), J. Exp. Med. 153, 629-639.
19. Pappas, M. G., R. Hajkowski and W. T. Hockmeyer (1983) J. Immunol. Methods 64, 205-214.
20. Ricciardi, R. P., Miller, J. S., and Roberts, B. E. (1979) Proc. Nat. Acad. Sci. USA 76, 4927-4931.
21. Sanderson, C. J., Thomas, J. A., and Twomey, C. E. (1980) Parasitology 80, 153-162.
22. Sanger, F. and Coulson, A. R.(1975) J. Mol. Bio. 94, 441.
23. Sanger, F., Nicklen, S. and Coulson, A. R. (1977) Proc. Nat. Acad. Sci. USA 74, 5463-5467.
24. Scharfstein, Julio, Rodriques, Mauricio Martins, Alves, Cesar Andrade, deSouza, Wanderley, Previato, Jose Osvaldo, and Mendonca-Previato, Lucia, (1983) J. Immunology 131, 972-976.
25. Schechter, M., A. Voller, C. J. Marikelle, J. E. Flint, F. Fuhl and M. A. Miles (1983) The Lancet 939-941.
26. Snary, D. and L. Hudson (1979), Fed. Eur. Biol. Soc. Letters 100, 166-170.
27. Snary, D., M. A., J. Ferguson, M. T. Scott and A. K. Allen (1981), Molec. Biochem Parasit 3, 345-356.
28. Spencer, H C., D. S. Allan, A. J. Sulzer and W. E. Collins (1980) Am. J. Trop. Med. Hyg. 29, 179-182.
29. Ullrich A., Shine, J., Chrigwin, J., Pictet, R., Tischer, E., Rutter, W. J., and Goodman, H. M. (1977) Science 196, 1313-1319.
30. Voller, A. and D. DeSavigny (1981) J. Immunol. Methods 46, 1-29.
31. Warren, L. G. (1960) J. Parasitology 46, 529-539.
32. Yanisch-Perron, C., Vieira, J. and Messing, J. (1985) Gene 34, 103-119.
33. Zingales, B., N. W. Andrews, V. Y. Kuwajima and W. Colli (1982), Molec. Biochem. Parasit 6, 111-124.
34. Zingales, B., N. F. Martin, R. M. DeLedekremer and W. Colli (1982), Fed. Eur. Biol. Soc. Letters 142, 238-242.
35. Voller et al., The Lancet, Feb. 22, 1975, 426-428.

We claim:

1. Antigenic material for the detection of Chagas' disease comprising a polypeptide or modification thereof having immunological cross-reactivity with Chagasic sera, said polypeptide having a molecular weight of approximately 70 kd, and an amino acid sequence as set forth in FIG. 4.

2. The antigenic material of claim 1, wherein said material is not immunologically reactive with sera from Leishmania infected patients.

3. The antigenic material of claims 1 or 2, wherein said polypeptide is synthesized by recombinant DNA technology.

4. The antigenic material of claims 1 or 2, essentially free of other proteins or polypeptides of *T. cruzi* origin.

5. The antigenic material of claims 1 or 2 synthesized by chemical means.

6. A method of detecting the presence of antibodies to Chagas' disease in the sera of a patient comprising contacting said sera with the antigenic material of claim 1 synthesized using recombinant technology and determining if an immunological reaction occurs therebetween.

7. A kit for diagnosing Chagas' disease comprising a container containing the antigen of claim 1.

8. A kit of claim 7 further comprising an additional container containing an enzyme-conjugated antibody.

9. A kit of claim 7 wherein the antigen is on latex beads.

10. Recombinant antigenic material for detection of Chagas' disease comprising a polypeptide or modification thereof having immunological cross-reactivity Chagasic sera, synthesized from a segment from a segment of nucleic acid encoding for a 70 kd protein as set forth in FIG. 4, said segment of nucleic acid being obtained from *T. cruzi*.

* * * * *

UNITED STATES PATENT AND TRADEMARK OFFICE
CERTIFICATE OF CORRECTION

PATENT NO. : 4,870,006
DATED : Sept. 26, 1989
INVENTOR(S) : Dragon et al.

It is certified that error appears in the above-identified patent and that said Letters Patent is hereby corrected as shown below:

Page 1 of 2

In column 1, line 14, please delete "881,419" and insert therefor --889,419--;

In column 2, line 58, please delete "70 kd 95 kd" and insert therefor --70 kd to 95 kd--;

In column 3, lines 60 and 61, please delete "renaturion" and insert therefor --renaturation--;

In column 3, lines 67 and 68, please delete "and 1 1 Brazilian" and insert therefor --and 1 Brazilian--;

In column 6, line 6, please delete "cipitation The" and insert therefor --cipitation. The--;

In column 7, line 15, please delete "Protein-" and insert therefor --Protein-A-Sepharose--;

In column 7, lines 28 and 29, please delete "polymerssseI" and insert therefor --polymeraseI--;

In column 8, line 68, please delete "toridase";

In column 8, line 68, please delete "lamb" and insert therefor --lamB gene--;

UNITED STATES PATENT AND TRADEMARK OFFICE
CERTIFICATE OF CORRECTION

PATENT NO. : 4,870,006

DATED : Sept. 26, 1989

INVENTOR(S) : Dragon et al.

It is certified that error appears in the above-identified patent and that said Letters Patent is hereby corrected as shown below:

In column 10, line 29, please delete "contemplated Any" and insert therefor --contemplated.  Any--;

Signed and Sealed this

Eleventh Day of December, 1990

Attest:

HARRY F. MANBECK, JR.

Attesting Officer

Commissioner of Patents and Trademarks